United States Patent
Yin et al.

(10) Patent No.: US 12,084,648 B2
(45) Date of Patent: Sep. 10, 2024

(54) RECOMBINANT BACTERIUM WITH A HIGH PHA YIELD AND THE CONSTRUCTION METHOD THEREOF

(71) Applicant: Shenzhen Bluepha Biosciences Co., Ltd., Shenzhen (CN)

(72) Inventors: Jin Yin, Shenzhen (CN); Yu Wang, Shenzhen (CN); Huayu Zhang, Shenzhen (CN); Yingzi Li, Shenzhen (CN)

(73) Assignee: Shenzhen Bluepha Biosciences Co., Ltd., Shenzhen (CN)

( * ) Notice: Subject to any disclaimer, the term of this patent is extended or adjusted under 35 U.S.C. 154(b) by 0 days.

(21) Appl. No.: 18/181,301

(22) Filed: Mar. 9, 2023

(65) Prior Publication Data

US 2023/0303966 A1    Sep. 28, 2023

(30) Foreign Application Priority Data

Mar. 22, 2022  (CN) .......................... 202210280731.0

(51) Int. Cl.
| | | |
|---|---|---|
| *C12N 1/20* | (2006.01) | |
| *C12N 15/78* | (2006.01) | |
| *C12P 7/625* | (2022.01) | |

(52) U.S. Cl.
CPC ............. *C12N 1/205* (2021.05); *C12N 15/78* (2013.01); *C12P 7/625* (2013.01)

(58) Field of Classification Search
None
See application file for complete search history.

(56) References Cited

U.S. PATENT DOCUMENTS

2021/0254028 A1    8/2021 Kobayashi et al.

FOREIGN PATENT DOCUMENTS

| CN | 108977890 A | 12/2018 |
|---|---|---|
| CN | 112368385 A | 2/2021 |
| EP | 2669365 A1 | 12/2013 |
| EP | 3101129 A1 | 12/2016 |
| JP | 2008-245633 A | 10/2008 |
| JP | 2015-077103 A | 4/2015 |
| JP | 2016-155936 A | 9/2016 |
| JP | 2017-077184 A | 4/2017 |
| KR | 10-2021-0152262 A | 12/2021 |
| WO | WO 2010/046221 A1 | 4/2010 |
| WO | WO 2018/021046 A1 | 2/2018 |
| WO | WO 2019/240155 A1 | 12/2019 |
| WO | WO 2021/206155 A1 | 10/2021 |

OTHER PUBLICATIONS

Arikawa et al. Microbial Cell Fact. 2016, 15:184, pp. 1-11.*
Decision of Reexamination issued in Chinese Application No. 202210280731.0, dated Sep. 5, 2022.
Decision of Rejection issued in Chinese Application No. 202210280731.0, dated Jun. 2, 2022.
First Office Action issued in Chinese Application No. 202210280731.0, dated Apr. 28, 2022.
Notification to Grant Patent Right for Invention issued in Chinese Application No. 202210280731.0, dated Sep. 20, 2022.
Second Office Action issued in Chinese Application No. 202210280731.0, dated May 16, 2022.
Search Report issued in Chinese Application No. 202210280731.0, dated Apr. 23, 2022.
Supplementary Search Report issued in Chinese Application No. 202210280731.0, dated Sep. 7, 2022.
Reese, C.B. "Oligonucleotide Synthesis. A Practical Approach", FEBS Letters, 188(1): 166-167, 1985.
Kunkel, T.A., "Oligonucleotide-Directed Mutagenesis without Phenotypic Selection", Current Protocols in Molecular Biology, Unit 8.1, 1987, in 2 pages.
Mullis, et al., *The Polymerase Chain Reaction*, Springer Science + Business Media, 1994, in 20 pages.
Sambrook, et al., *Molecular Cloning, A Laboratory Manual*, 2nd Ed., Cold Spring Harbor Laboratory Press, 1989, in 426 pages.
Smith et al., *March's Advanced Organic Chemistry: Reactions, Mechanisms, and Structure*, 6th Ed., Wiley-Interscience, 2007, in 19 pages.
Budde et al., "Production of Poly(3-Hydroxybutyrate-co-3-Hydroxyhexanoate) from Plant Oil by Engineered *Ralstonia eutropha* Strains", Applied and Environmental Microbiology, 2011, 77(9): 2847-2854.
Extended European Search Report issued in EP Application No. 23158486.3, dated Sep. 11, 2023.
Notice of Allowance issued in Japanese Application No. 2023-020128, dated Jul. 11, 2023.
Office Action issued in Japanese Application No. 2023-020128, dated Apr. 13, 2023.

* cited by examiner

*Primary Examiner* — Vera Afremova
(74) *Attorney, Agent, or Firm* — Knobbe, Martens, Olson & Bear, LLP

(57) ABSTRACT

A recombinant bacterium with a high PHA yield and its construction method provide an engineered microorganism that can be used for the production of polyhydroxyalkanoate (PHA). A recombinant *Ralstonia eutropha* with a high PHA yield includes a promoter for upregulating a phaJ gene and further includes a mutant phaC gene. The recombinant *Ralstonia eutropha* can be used for producing 3-hydroxybutyrate-co-3-hydroxyhexanoate (PHBHHx) in PHA.

4 Claims, 1 Drawing Sheet
Specification includes a Sequence Listing.

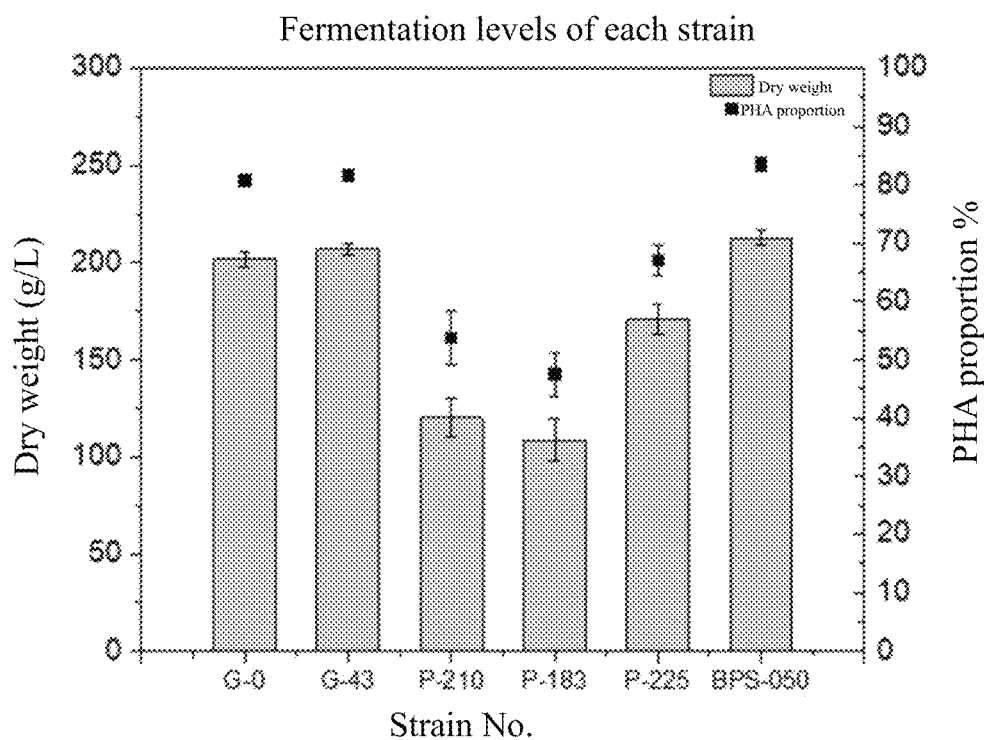

RECOMBINANT BACTERIUM WITH A HIGH PHA YIELD AND THE CONSTRUCTION METHOD THEREOF

SEQUENCE LISTING IN ELECTRONIC FORMAT

The present application is being filed along with an Electronic Sequence Listing in ST.26 format. The Electronic Sequence Listing is provided as a file entitled CNKH039_001AUS_SL_xml created and last saved on Jan. 6, 2023, which is approximately 35.7 KB in size. The information in the Electronic Sequence Listing is incorporated herein by reference in its entirety in accordance with 35 U.S.C. § 1.52(e).

Deposit of Microorganism

*Ralstonia eutropha* Re0980 has been deposited on Dec. 31, 2021 at the independent administrative agency, Guangdong Microbial Culture Collection (Institute of Microbiology, Guangdong Academy of Sciences No. 59 Building, No. 100 Xianlie Zhong Road, Yuexiu District, Guangzhou 510070, PR China) with an accession number of GDMCC62177 under the provisions of the Budapest Treaty on the International Recognition of the Deposit of Microorganisms for the Purposes of Patent Procedure.

BPS-050 has been deposited on Oct. 13, 2021 at the independent administrative agency, China General Microbiological Culture Collection Center (Institute of Microbiology Chinese Academy of Sciences, No. 1 West Beichen Road Chaoyang District Beijing China) with an accession number of CGMCC23600 under the provisions of the Budapest Treaty on the International Recognition of the Deposit of Microorganisms for the Purposes of Patent Procedure.

The deposits above were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposits above will be made available by Guangdong Microbial Culture Collection and China General Microbiological Culture Collection Center under the terms of the Budapest Treaty, and subject to an agreement between Applicant and Guangdong Microbial Culture Collection and China General Microbiological Culture Collection Center which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

Technical Field

The present invention belongs to the field of genetic engineering and fermentation engineering, and more particularly, the present invention relates to a recombinant bacterium with high polyhydroxyalkanoate (PHA) yield, the preparation method and use thereof.

Background Art

Polyhydroxyalkanoates (PHAs) are a class of renewable and degradable polymers synthesized by microorganisms with multiple material properties that have a wide range of application prospects in the fields of medicine, materials and environmental protection. Polyhydroxyalkanoates are widely present in microbial cells, mainly acting act as carbon sources and energy storage carriers. According to the difference of monomer type and polymerization mode, PHAs have a series of material properties with diversity from hard and brittle hard plastic to soft elastomer.

Polyhydroxybutyrate (PHB) is a commercially useful composite biopolymer that is an intracellular material produced by a large number of bacteria. Polyhydroxybutyrate is a useful biomaterial based on the chemical and physical properties of polymers with a variety of potential applications, including use as a biodegradable/thermoplastic material, as a source of chiral centers for the organic synthesis of certain antibiotics, and as a matrix for drug delivery and bone replacement. 3-hydroxybutyrate-co-3-hydroxyhexanoate (PHBHHx) is one of the PHA that exists in the cytoplasm as insoluble, microspheroidal particles.

*Ralstonia eutropha* (also known as *Cupriavidus necator*) is an important model bacterium for studying the synthesis of polyhydroxyalkanoate (PHA), and it is the strain used for PHB strain production that has been studied more recently. When carbon is in excess and nitrogen is in deficiency, the strain can accumulate PHB in large amount; however, when other intracellular carbon sources are highly metabolized, the synthesis of PHB will be affected.

The synthesis pathway of PHB in *Ralstonia eutropha* has been elucidated clearly. Acetoacetyl-CoA was synthesized by Acyl-CoA under the action of phaA (β-ketothiolase), and then 3-hydroxybutyric acid was synthesized by phaB (Acetoacetyl-CoA reductase). At the same time, 3-hydroxycaproic acid was produced through dehydrogenation by phaJ ((R)-enoyl-CoA hydratase), and two compounds were polymerized under the action of phaC (PHA polymerase) to form PHBHHx.

In order to produce PHBHHx more efficiently and control the molar ratio of the 3-hydroxycaproic acid monomer therein at a specific proportion, it is urgent to develop a novel microorganism for the synthesis of PHA.

SUMMARY

The present invention meets the above requirement in the art by providing a recombinant *Ralstonia eutropha* with a high PHA yield. In the present invention, *Ralstonia eutropha* H16 (deposited in China General Microbiological Culture Collection Center with a deposit number of CGMCC 1.7092) is used as an original strain, and the strain is further modified to further improve its fermentation performance.

In one aspect, the present invention provides a recombinant *Ralstonia eutropha*, wherein a promoter for upregulating a phaJ gene is introduced into the genome of the recombinant *Ralstonia eutropha*, and the recombinant *Ralstonia eutropha* includes an introduced phaC mutant gene. In the recombinant *Ralstonia eutropha* provided by the present invention, the expression of the introduced phaC mutant gene enables the recombinant *Ralstonia eutropha* to synthesize 3-hydroxybutyrate-co-3-hydroxyhexanoate. In one embodiment of the present invention, the proportion of 3-hydroxycaproic acid in the 3-hydroxybutyrate-co-3-hydroxyhexanoate produced by the recombinant *Ralstonia eutropha* is increased.

In some embodiments of this aspect of the present invention, a promoter for upregulating the phaJ gene is introduced into the genome of the recombinant *Ralstonia eutropha* by way of homologous recombination. In a preferred embodiment of the present invention, a promoter sequence upregulating the phaJ gene is inserted upstream of the phaJ gene by homologous recombination using a plasmid with the promoter sequence. In the recombinant *Ralstonia eutropha* provided by the present invention, the phaJ gene is preferably a phaJ4b gene. Still preferably, the promoter sequence is selected from the group consisting of a phaJ43 promoter sequence of SEQ ID NO: 3, a phaJ210 promoter sequence of SEQ ID NO: 8, a phaJ183 promoter sequence of SEQ ID NO: 9 and a phaJ225 promoter sequence of SEQ ID NO: 10; more preferably, the promoter sequence is the phaJ43 promoter sequence of SEQ ID NO: 3.

In some embodiments of this aspect of the present invention, the recombinant *Ralstonia eutropha* includes an introduced phaC mutant gene. In a preferred embodiment, the phaC mutant gene is introduced by the following methods: (1) the introduced phaC mutant gene is integrated into the genome of the recombinant *Ralstonia eutropha* and inactivating the original genomic phaC gene, wherein the method of inactivation can include mutation, substitution, replacement or knockout, preferably the inactivation is carried out by construction of a plasmid for phaC gene knockout, the specific sequence of the original genomic phaC gene is represented by SEQ ID NO: 1; or (2) the introduced phaC mutant gene is present on a stable plasmid introduced into the recombinant *Ralstonia eutropha*; wherein preferably the sequence of the introduced phaC mutant gene is represented by SEQ ID NO: 5.

In a preferred embodiment of this aspect of the present invention, the recombinant *Ralstonia eutropha* can further include a proC gene introduced therein. In particular, when the introduced phaC mutant gene is present on a stable plasmid introduced into the recombinant *Ralstonia eutropha*, the original genomic phaC gene and the proC gene are inactivated while the proC gene is introduced on a plasmid stably existing in the recombinant *Ralstonia eutropha*, wherein the method of inactivation can include mutation, substitution, replacement or knockout, preferably the inactivation is carried out by construction of a plasmid for proC gene knockout, the specific sequence of the original genomic proC gene is represented by SEQ ID NO: 2; wherein preferably, the sequence of the introduced proC gene is represented by SEQ ID NO: 4.

In a preferred embodiment of this aspect of the present invention, *Ralstonia eutropha* is used as an original strain for the recombinant *Ralstonia eutropha*. Preferably, the original strain is *Ralstonia eutropha* H16; more preferably, the original strain is *Ralstonia eutropha* Re0980.

In a preferred embodiment of this aspect of the present invention, a promoter for upregulating the phaJ gene is introduced into the genome of the recombinant *Ralstonia eutropha*, preferably the sequence of the promoter is the phaJ43 promoter sequence of SEQ ID NO: 3; and the original genomic phaC and proC genes are knocked out, specifically, the sequence of the original genomic phaC gene is represented by SEQ ID NO: 1, and specifically, the sequence of the original genomic proC gene is represented by SEQ ID NO: 2; a plasmid stably existing in *Ralstonia eutropha* is further introduced into the recombinant *Ralstonia eutropha*, and the plasmid is loaded with an introduced phaC mutant gene and an introduced proC gene, wherein preferably the introduced phaC mutant gene sequence is represented by SEQ ID NO: 5, and preferably the introduced proC gene sequence is represented by SEQ ID NO: 4.

In a preferred embodiment of this aspect of the present invention, the recombinant *Ralstonia eutropha* strain BPS-050 is deposited in China General Microbiological Culture Collection Center (Address: Building 3, NO. 1 Courtyard, West Beichen Road, Chaoyang District, Beijing, Institute of Microbiology, Chinese Academy of Sciences, postal code: 100101) on Oct. 13, 2021 with a deposit number of CGMCC No. 23600.

Another aspect of the present invention further provides a method for preparing a recombinant *Ralstonia eutropha*, which includes the following steps: introducing a promoter for upregulating the phaJ gene into the genome of the *Ralstonia eutropha* using *Ralstonia eutropha* as an original strain, and introducing a phaC mutant gene into the *Ralstonia eutropha*, so as to obtain the recombinant *Ralstonia eutropha* producing 3-hydroxybutyrate-co-3-hydroxyhexanoate with an increased ratio of 3-hydroxycaproic acid, wherein the expression of the introduced phaC mutant gene enables the recombinant *Ralstonia eutropha* to synthesize 3-hydroxybutyrate-co-3-hydroxyhexanoate, In some embodiments of this aspect of the present invention, the promoter upregulating the phaJ gene is introduced into the genome of the recombinant *Ralstonia eutropha* by way of homologous recombination. In a preferred embodiment of the present invention, the promoter sequence is inserted upstream of the phaJ gene by homologous recombination to upregulate the phaJ gene, using a plasmid with the promoter sequence. Preferably, the phaJ gene is a phaJ4b gene. Still preferably, the promoter sequence is selected from the group consisting of the phaJ43 promoter sequence of SEQ ID NO: 3, the phaJ210 promoter sequence of SEQ ID NO: 8, the phaJ183 promoter sequence of SEQ ID NO: 9 and the phaJ225 promoter sequence of SEQ ID NO: 10; more preferably, the promoter sequence is a phaJ43 promoter sequence.

In some embodiments of this aspect of the present invention, the phaC mutant gene is introduced into the recombinant *Ralstonia eutropha*. In a preferred embodiment, the phaC mutant gene is introduced by the following methods: (1) introducing the phaC mutant gene by integrating the phaC mutant gene into the genome of the recombinant *Ralstonia eutropha* and inactivating the original genomic phaC gene, wherein the method of inactivation can include mutation, substitution, replacement or knockout, preferably by the construction of a plasmid for phaC gene knockout, specifically the sequence of the original genomic phaC gene is represented by SEQ ID NO: 1; or (2) introducing the phaC mutant gene by loading the phaC mutant gene on a stable plasmid and introducing it into the recombinant *Ralstonia eutropha*; wherein preferably, the sequence of the introduced phaC mutant gene is represented by SEQ ID NO: 5.

In a preferred embodiment of this aspect of the present invention, it is further included introducing the proC gene into the recombinant *Ralstonia eutropha*. In particular, when the introduced phaC mutant gene is present on a stable plasmid introduced into the recombinant *Ralstonia eutropha*, the original genomic phaC and proC genes are inactivated, while the proC gene on the stable plasmid is introduced into the recombinant *Ralstonia eutropha*, wherein the method of inactivation can include mutation, substitution, replacement or knockout, preferably the inactivation is carried out by construction of a plasmid for proC gene knockout, specifically the sequence of the original genomic proC gene is represented by SEQ ID NO: 2; wherein preferably, the sequence of the introduced proC gene is represented by SEQ ID NO: 4; still further preferably, the introduced phaC mutant gene and the introduced proC gene are loaded on the same plasmid.

In a preferred embodiment of this aspect of the present invention, the original strain is *Ralstonia eutropha* H16, preferably the original strain is *Ralstonia eutropha* Re0980.

In a preferred embodiment of this aspect of the present invention, the method includes the following steps:
(1) taking *Ralstonia eutropha* as an original strain, knocking out original genomic phaC and proC genes, preferably said knocking out is carried out by the construction of a phaC knockout plasmid and a proC knockout plasmid, respectively, specifically the original genomic phaC gene sequence is represented by SEQ ID NO: 1 and specifically the original genomic proC gene sequence is represented by SEQ ID NO: 2;
(2) introducing a promoter for upregulating the phaJ gene into the genome of the *Ralstonia eutropha*, preferably the sequence of the promoter is a phaJ43 promoter sequence of SEQ ID NO: 3;
(3) introducing a plasmid stably existing in *Ralstonia eutropha*, wherein the plasmid is loaded with an introduced phaC mutant gene and/or an introduced proC gene, wherein preferably the sequence of the introduced phaC mutant gene is represented by SEQ ID NO: 5, and preferably the sequence of the introduced proC gene is represented by SEQ ID NO: 4;
more preferably, the original strain is *Ralstonia eutropha* Re0980.

The present invention also provides the use of a recombinant *Ralstonia eutropha* for the preparation of PHA and/or PHB. In a preferred embodiment, the present invention provides the use of the recombinant *Ralstonia eutropha* as described herein or prepared by the methods described herein for the preparation of PHA and/or PHB.

The present invention also provides a method for preparing PHA and/or PHB, which includes the steps of obtaining PHA or PHB through fermentation by using the recombinant *Ralstonia eutropha* described herein or the recombinant *Ralstonia eutropha* prepared by the method described herein.

BRIEF DESCRIPTION OF THE DRAWINGS

FIG. 1 shows the culture results of each strain.

DETAILED DESCRIPTION OF THE PREFERRED EMBODIMENTS

Unless otherwise indicated, the practice of the present invention will employ conventional techniques of molecular biology (including recombinant techniques), microbiology, cell biology, biochemistry and synthetic biology, and the like, which are within the skill of the art. Such techniques are well explained in the literatures: "Molecular Cloning: A Laboratory Manual," 2nd ed. (Sambrook et al., 1989); "Oligonucleotide Synthesis" (edited by M. J. Gait, 1984); "Animal Cell Culture" (edited by R. I. Freshney, 1987); "Methods in Enzymology" (Academic Press, Inc.); "Current Protocols in Molecular Biology" (F. M. Ausubel et al., 1987, and updated regularly); "PCR: The Polymerase Chain Reaction," (edited by Mullis et al., 1994); Singleton et al., Dictionary of Microbiology and Molecular Biology 2nd ed., J. Wiley & Sons (New York, N.Y. 1994); and March's Advanced Organic Chemical Reactions, Mechanisms and Structure, 4th ed., John Wiley & Sons (New York, N.Y. 1992), which provide a person skilled in the art with a general guide for many of terms used in the present application.

Unless otherwise defined, all technical and scientific terms used herein have the same meaning as commonly understood by one of ordinary skill in the art to which the present invention pertains. For the purposes of the present invention, the following terms are defined below.

The articles "a/an" and "this/the" as used herein refer to one or more (i.e., at least one) grammatical object of the article. For example, "an element" means one or more element.

The use of alternatives (such as "or") is to be understood to mean either, both, or any combination thereof.

The term "and/or" should be understood to mean either or both of the alternatives.

As used herein, the term "about" or "approximately" refers to the number, level, value, quantity, frequency, percentage, scale, size, amount, weight, or length that is changed by up to 15%, 10%, 9%, 8%, 7%, 6%, 5%, 4%, 3%, 2%, or 1% as compared to a reference number, level, value, quantity, frequency, percentage, scale, size, amount, weight, or length. In one embodiment, the term "about" or "approximately" refers to a range of numbers, levels, values, quantities, frequencies, percentages, scales, sizes, amounts, weights, or lengths of ±15%, ±10%, ±9%, ±8%, ±7%, ±6%, ±5%, ±4%, ±3%, ±2%, or ±1% surrounding a reference number, level, value, quantity, frequency, percentage, scale, size, amount, weight, or length.

As used herein, the term "substantially/essentially" refers to a number, level, value, quantity, frequency, percentage, scale, size, amount, weight, or length of about 90%, 91%, 92%, 93%, 94%, 95%, 96%, 97%, 98%, or 99% or more as compared to a reference number, level, value, quantity, frequency, percentage, scale, size, amount, weight, or length. In one embodiment, that term "substantially the same" refers to a range of number, level, value, quantity, frequency, percentage, scale, size, amount, weight, or length that is about the same as the reference number, level, value, quantity, frequency, percentage, scale, size, amount, weight, or length.

As used herein, the term "substantially free" when used to describe a composition, such as a population of cells or a culture medium, refers to a composition that is free of a specified substance, e.g., 95% free, 96% free, 97% free, 98% free, 99% free of a specified substance, or a composition in which the specified substance is undetectable as measured by conventional means. A similar meaning may be applied to the term "absent" when it refers to the absence of a specific substance or component of the composition.

Throughout this specification, the terms "comprise", "include", "contain", and "have" are to be understood as implying the inclusion of a stated step or element or group of steps or elements, but not excluding any other step or element or group of steps or elements, unless the context requires otherwise. In certain embodiments, the terms "comprise", "include", "contain", and "have" are used synonymously.

"Consisting of" means including but limited to anything after the phrase "consisting of". Thus, the phrase "consisting of" indicates that the listed elements are required or mandatory, and that no other elements may be present.

"Consisting essentially of" means including any elements listed after the phrase "consisting essentially of" and is limited to other elements that do not interfere with or contribute to the activities or acts specified in the disclosure of the listed elements. Thus, the phrase "consisting essentially of" indicates that the listed elements are required or mandatory, but that no other elements are optional, and may or may not be present depending on whether they affect the activities or acts of the listed elements.

Throughout this specification, references to "one embodiment", "some embodiments", "a specific embodiment", and other similar expressions, mean that a particular feature, structure, or characteristic described in connection with the embodiment is included in at least one embodiment of the present invention. Accordingly, the appearances of the foregoing phrases in various places throughout this specification are not necessarily all referring to the same embodiment. Furthermore, the particular feature, structures, or characteristic may be combined in any suitable manner in one or more embodiments.

When the features relating to a particular aspect of the present invention (such as the product of the present invention) are disclosed, such disclosure is also considered applicable to any other aspect of the present invention (e.g., the method and use of the present invention), with the necessary modifications.

In order to achieve the object of the present invention, the key points of the solution provided by the present invention lie in:

There is no promoter upstream of the original phaJ4b gene of *Ralstonia eutropha*. The inventor has found that the overexpression of the phaJ4b gene can be realized by inserting an exogenous promoter, and the proportion of HHx in PHBHHx can be increased. For example, in the genome of *Ralstonia eutropha*, a specific promoter sequence is inserted upstream of the phaJ gene by homologous recombination to upregulate the phaJ gene, using a plasmid with a specific promoter.

On the other hand, the original phaC gene of *Ralstonia eutropha* cannot synthesize PHBHHx, and a phaC mutant gene needs to be introduced into the *Ralstonia eutropha* to realize the synthesis of PHBHHx, especially the synthesis of PHBHHx when grease is used as a carbon source.

For the phaC mutant gene, the phaC mutant gene can be introduced into *Ralstonia eutropha* in two ways and stably expressed:
(1) inactivating the original genomic phaC gene and integrating the phaC mutant gene into the genome through homologous recombination; or
(2) inactivating the original genomic phaC gene, and constructing a plasmid with the phaC mutant gene and transforming the plasmid into the recombinant strain.

Stable expression of the plasmid can be achieved by carrying a essential gene for strain growth in the plasmid while inactivating the gene for synthesis in the genome. The essential gene may be, for example, a proC gene.

More specifically, the present invention provides a *Ralstonia eutropha* mutant strain, the mutant strain has the original genomic phaC and proC genes knocked out, an introduced promoter for upregulating the phaJ gene, and a plasmid capable of stably existing in *Ralstonia eutropha* introduced simultaneously, wherein the plasmid is loaded with the phaC mutant gene and the proC gene.

Another object of the present invention is to provide a method for constructing a strain with high PHBHHx yield, the steps thereof are as follows:
1. Constructing a plasmid for phaC gene knockout, and knocking out the phaC gene in *Ralstonia eutropha*, and the specific sequence of the knocked-out gene is represented by SEQ ID NO: 1.
2. Constructing a plasmid for proC gene knockout, and further knocking out the genomic proC gene in the *Ralstonia eutropha* in step 1, and the specific sequence of the knocked-out gene is represented by SEQ ID NO: 2.
3. Designing a promoter sequence for upregulating the phaJ gene, constructing an insertion plasmid for upregulating the phaJ gene, and further modifying the *Ralstonia eutroph* obtained in step 2 by inserting the designed promoter for upregulating the phaJ gene, and the specific sequence of the inserted gene sequence is represented by SEQ ID NO: 3.
4. Constructing a stable plasmid with an exogenous phaC mutant gene and a proC gene, and transforming the stable plasmid into the *Ralstonia eutroph* in step 3 to supplement and construct a complete PHB pathway.

The present invention also provides a polymer produced by using the above strain for producing PHBHHx.

In some embodiments, the microorganism of the present invention for producing PHA is *Ralstonia eutropha* or a related strain thereof. In a specific embodiment, the microorganism of the present invention for producing PHA is *Ralstonia eutropha* H16 or derived from *Ralstonia eutropha* H16.

Further, the present invention provides a novel strain BPS-050 obtained by the above genetic engineering method, which is deposited in China General Microbiological Culture Collection Center on Oct. 13, 2021 with a deposit number of CGMCC No. 23600.

The morphological characteristics of strain BPS-050 are as follows: the colonies were observed to be pale yellow on LB solid medium, with neat edges, smooth and moist; with strong odor. Microscopic examination showed that the strain is Gram-negative, short-rod-shaped, and asporous.

The 16s RNA sequence of the strain BPS-050 is as follows:

```
AGGGCTTTGGCGGCTGCCTTAACATGCAAGTCGAACGGCAGCACGGGCTT
CGGCCTGGTGGCGAGTGGCGAACGGGTGAGTAATACATCGGAACGTGCCC
TGTAGTGGGGGATAACTAGTCGAAAGATTAGCTAATACCGCATACGACCT
GAGGGTGAAAGCGGGGGACCGCAAGGCCTCGCGCTACAGGAGCGGCCGAT
GTCTGATTAGCTAGTTGGTGGGGTAAAAGCCTACCAAGGCGACGATCAGT
AGCTGGTCTGAGAGGACGATCAGCCACACTGGGACTGAGACACGGCCCAG
ACTCCTACGGGAGGCAGCAGTGGGGAATTTTGGACAATGGGGGCAACCCT
GATCCAGCAATGCCGCGTGTGTGAAGAAGGCCTTCGGGTTGTAAAGCACT
TTTGTCCGGAAAGAAATGGCTCTGGTTAATACCCGGGGTCGATGACGGTA
CCGGAAGAATAAGCACCGGCTAACTACGTGCCAGCAGCCGCGGTAATACG
TAGGGTGCGAGCGTTAATCGGAATTACTGGGCGTAAAGCGTGCGCAGGCG
GTTTTGTAAGACAGGCGTGAAATCCCCGAGCTCAACTTGGGAATGGCGCT
TGTGACTGCAAGGCTAGAGTATGTCAGAGGGGGGTAGAATTCCACGTGTA
GCAGTGAAATGCGTAGAGATGTGGAGGAATACCGATGGCGAAGGCAGCCC
CCTGGGACGTCACTGACGCTCATGCACGAAAGCGTGGGGAGCAAACAGGA
TTAGATACCCTGGTAGTCCACGCCCTAAACGATGTCAACTAGTTGTTGGG
GATTCATTTCTTCAGTAACGTAGCTAACGCGTGAAGTTGACCGCCTGGGG
AGTACGGTCGCAAGATTAAAACTCAAAGGAATTGACGGGGACCCGCACAA
```

-continued

```
GCGGTGGATGATGTGGATTAATTCGATGCAACGCGAAAAACCTTACCTAC

CCTTGACATGCCACTAACGAAGCAGAGATGCATTAGGTGCCCGAAAGGGA

AAGTGGACACAGGTGCTGCATGGCTGTCGTCAGCTCGTGTCGTGAGATGT

TGGGTTAAGTCCCGCAACGAGCGCAACCCTTGTCTCTAGTTGCTACGAAA

GGGCACTCTAGAGAGACTGCCGGTGACAAACCGGAGGAAGGTGGGGATGA

CGTCAAGTCCTCATGGCCCTTATGGGTAGGGCTTCACACGTCATACAATG

GTGCGTACAGAGGGTTGCCAACCCGCGAGGGGAGCTAATCCCAGAAAAC

GCATCGTAGTCCGGATCGTAGTCTGCAACTCGACTACGTGAAGCTGGAAT

CGCTAGTAATCGCGGATCAGCATGCCGCGGTGAATACGTTCCCGGGTCTT

GTACACACCGCCCGTCACACCATGGGAGTGGGTTTTGCCAGAAGTAGTTA

GCCTAACCGCAAGGAGGGCGATACCACGGCAGGTCATACTATCC.
```

In some embodiments, the original genomic phaC gene of *Ralstonia eutropha* may include, consist essentially of, or consist of: a nucleotide sequence shown by SEQ ID NO: 1 or a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or a range consisting of any two of the foregoing values of identity with SEQ ID NO: 1.

In some embodiments, the phaC mutant gene for introduction into *Ralstonia eutropha* may include, consist essentially of, or consist of: a nucleotide sequence shown by SEQ ID NO: 5 or a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or a range consisting of any two of the foregoing values of identity with SEQ ID NO: 5.

In some embodiments, the proC described herein is a phaC in the genome of *Ralstonia eutropha*. In some embodiments, the proC gene in *Ralstonia eutropha* may include, consist essentially of, or consist of: a nucleotide sequence shown by SEQ ID NO: 2 or a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or a range consisting of any two of the foregoing values of identity with SEQ ID NO: 2.

In some embodiments, the proC gene for introduction into *Ralstonia eutropha* herein may include, consist essentially of, or consist of: a nucleotide sequence shown by SEQ ID NO: 4 or a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or a range consisting of any two of the foregoing values of identity with SEQ ID NO: 4.

In some embodiments, the phaJ43 promoter sequence used herein may include, consist essentially of, or consist of: a nucleotide sequence shown by SEQ ID NO: 3 or a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% or a range consisting of any two of the foregoing values of identity with SEQ ID NO: 3.

In some embodiments, the one or more enzymes used in the present invention may be a mutant or variant of the enzymes described herein. As used herein, "mutant" and "variant" refer to molecules that retain the same or substantially the same biological activity as the original sequence. The mutant or variant may be from the same or different species, or may be synthetic sequences based on natural molecules or existing molecules. In some embodiments, the terms "mutant" and "variant" refer to that a polypeptide has an amino acid sequence that differs from the corresponding wild-type polypeptide by at least one amino acid. For example, a mutant and variant may include a conservative amino acid substitution, i.e., replacement of an original corresponding amino acids with an amino acid having similar properties. Conservative substitution may be substitution of a polar amino acid with a polar amino acid (glycine (G, Gly), serine (S, Ser), threonine (T, Thr), tyrosine (Y, Tyr), cysteine (C, Cys), asparagine (N, Asn) and glutamine (Q, Gln)); substitution of a nonpolar amino acid with a nonpolar amino acid (alanine (A, Ala), valine (V, Val), tryptophan (W, Trp), leucine (L, Leu), proline (P, Pro), methionine (M, Met) and phenylalanine (F, Phe)); substitution of an acidic amino acid with an acidic amino acid (aspartic acid (D, Asp), glutamic acid (E, Glu)); substitution of a basic amino acid with a basic amino acid (arginine (R, Arg), histidine (H, His) and lysine (K, Lys)); substitution of a charged amino acid with a charged amino acid (Aspartic acid (D, Asp), glutamic acid (E, Glu), histidine (H, His), lysine (K, Lys) and arginine (R, Arg)); and substitution of a hydrophobic amino acid with a hydrophobic amino acid (Alanine (A, Ala), leucine (U, Leu), isoleucine (I, Ile), Valine (V, Val), proline (P, Pro), phenylalanine (F, Phe), tryptophan (W, Trp) and Methionine (M, Met)). In some other embodiments, a mutant or variant may also include a non-conservative substitution.

In some embodiments, the mutant or variant polypeptide may have substitution, addition, insertion or deletion of about 1, 2, 3, 4, 5, 6, 7, 8, 9, 10, 15, 20, 30, 40, 50, 60, 70, 80, 90, 100 or more or a range consisting of any two of the foregoing values of amino acids. Compared with the unmodified enzyme, the mutant or variant may have an activity of at least 40%, 45%, 50%, 55%, 60%, 65%, 70%, 75%, 80%, 85%, 90%, 91%, 92%, 93%, 94%, 95%, 96%, 97%, 98%, 99% or 100%, or a range consisting of any two of the foregoing values. The enzyme activity may be determined by conventional techniques known in the art, such as a colorimetric enzymatic assay.

As is well known to a person skilled in the art, expression of a heterologous nucleic acid in a host can be improved by having one or more encoding nucleotides (i.e., codons) in a nucleotide sequence encoding a polypeptide, such as an enzyme, replaced by another codon that is better expressed in the host (i.e., codon optimization). One reason for this effect is that different organisms show preference for different codons. In some embodiments, the nucleotide sequences disclosed herein encoding a polypeptide such as an enzyme are modified or optimized such that the resulting nucleotide sequences reflect codon preference for a particular host.

A polynucleotide or polypeptide has a certain percentage of "sequence identity" or "identity" with another polynucleotide or polypeptide means that when two sequences are aligned, the specified percentage of bases or amino acids are the same and in the same relative position. Determining identity percentage of two amino acid sequences or two nucleotide sequences may include aligning and comparing amino acid residues or nucleotides at corresponding positions in the two sequences. If all positions in the two sequences are occupied by the same amino acid residues or nucleotides, then said sequences are considered to be 100% identical. Sequence identity can be determined in various different ways, for example, sequences can be aligned using a variety of methods and computer programs (for example, BLAST, T-COFFEE, MUSCLE, MAFFT and the like).

Some embodiments of the present invention relate to expression constructs containing a nucleotide sequence of a phaJ gene promoter, for example, vectors, such as plasmids, preferably expression constructs containing a nucleotide sequence encoding the phaJ gene promoter. The nucleotide sequence encoding the phaJ gene promoter is as described above. Preferably, the expression construct is a plasmid. Preferably, the expression construct may be used to express the phaJ gene promoter in *Ralstonia eutropha*, preferably in *Ralstonia eutropha* H16.

Some embodiments of the present invention relate to expression constructs containing one or more nucleotide sequences encoding phaC and/or proC, for example, vectors, such as plasmids, preferably expression constructs containing one or more nucleotide sequences encoding phaC and/or proC. The nucleotide sequences encoding phaC and/or proC are as described above. Preferably, the expression construct is a plasmid. Preferably, the expression construct can be used to express phaC and/or proC, more preferably co-express phaC and proC in *Ralstonia eutropha*, preferably in *Ralstonia eutropha* H16.

Engineering a microorganism may include expressing an enzyme of interest in the microorganism. In some embodiments, the expression constructs described herein are introduced into a host microorganism by transformation to express an enzyme of interest. The transformation may be carried out by methods known in the art. For example, a plasmid containing a nucleotide sequence encoding a phaJ gene promoter, phaC, and/or proC as described herein may be introduced into *Ralstonia eutropha* by transformation to express the phaJ gene promoter, phaC, and/or proC. The transformation may be, but is not limited to, *Agrobacterium*-mediated transformation, electroporation with plasmid DNA, DNA uptake, gene gun transformation, virus-mediated transformation or protoplast transformation. Transformation may be any other transformation method suitable for a particular host.

Expression of an enzyme of interest in a host microorganism to achieve the intended purpose may be achieved as described above by transforming an expression construct encoding the enzyme into the host microorganism, or by incorporating the expression construct encoding the enzyme into the genomic sequence of the host microorganism in a variety of ways, or by enhancing transcription and/or expression of an enzyme-encoding gene native to the host microorganism in a variety of ways, such as by using stronger regulatory elements such as promoters. Such a manner is generally well known to a person skilled in the art.

Engineering a microorganism may include interfering with the function of a protein of interest in the microorganism, e.g., reducing or eliminating expression of the protein, which may be achieved, for example, by deletion, substitution or knockout of a genomic sequence of interest in the microorganism. In some embodiments, the genomic genes of phaC and/or proC in the microorganisms described herein are deleted, replaced, or knocked out. In some embodiments, the sequence of the phaC gene that is deleted, replaced, or knocked out is as represented by SEQ ID NO: 1. In some embodiments, the sequence of the proC gene that is deleted is as represented by SEQ ID NO: 2. Preferably, inactivation of the genomic phaC and/or proC gene is achieved by knockout.

In addition to deletion of the genomic sequence of interest in the microorganism, the function of the protein of interest may be interfered with by other methods known in the art, including, but not limited to, interfering with transcription of a genomic sequence encoding the protein of interest, interfering with expression of mRNA encoding the protein of interest, interfering with delivery of the protein of interest, such as delivery out of a cell; more specifically, include, but not limited to, methods of causing the deletion of all or part of a genomic sequence encoding a protein of interest or a regulatory element thereof such as a promoter, inserting one or more nucleotides affecting the transcription thereof such as a stop codon in the middle of a genomic sequence encoding a protein of interest or a regulatory element thereof such as a promoter, or mutating one or more nucleotides thereof to the extent that said genomic sequence is not properly transcribed, introducing reagents that interfere with or silence the mRNA encoding a protein of interest such as siRNA or dsRNAi reagents, or methods that inhibit or stop the function of a system (e.g., chaperone protein, signal sequence, transporter protein) that delivers a protein of interest, for example, outside a cell.

Suitable medium for host culture may include standard medium (for example Luria-Bertani broth, optionally supplemented with one or more other reagents, such as inducers; standard yeast medium and the like). In some embodiment, the medium may be supplemented with fermentable sugar (for example hexoses, such as glucose, xylose and the like). In some embodiments, a suitable medium contains an inducer. In certain such embodiments, the inducer includes rhamnose.

The carbon sources in a suitable medium for host culture may vary from simple sugars such as glucose to more complex hydrolysates of other biomass such as yeast extracts. The addition of salts generally provides the necessary elements such as magnesium, nitrogen, phosphorus and sulfur to allow for cellular synthesis of polypeptides and nucleic acids. Suitable medium may also be supplemented with selective reagents, such as antibiotics, to selectively maintain certain plasmids and the like. For example, if the microorganism is resistant to a certain antibiotic such as ampicillin, tetracycline or kanamycin, the antibiotic may be added to the medium to prevent the growth of cells lacking resistance. Suitable medium may be supplemented with other compounds as needed to select for desired physiological or biochemical properties, such as specific amino acids and the like.

Materials and methods for the maintenance and growth of microorganisms suitable for the present invention are described herein, for example, in the Example section.

For small-scale production, the engineered microorganisms may be made to grow in batches of, for example, about 100 mL, 500 mL, 1 L, 5 L or 10 L, ferment, and express desired nucleotide sequences upon induction, such as a nucleotide sequence encoding phaC and/or proC, and/or synthesize desired fermentation products, such as PHA and/or PHB. For mass production, the engineered microorganisms may be made to grow in batches of about 10 L, 100 L, 1000 L, 10,000 L, 100,000 L or greater, ferment, and express desired nucleotide sequences upon induction, such as a nucleotide sequence encoding phaC and/or proC, and/or synthesize desired fermentation products, such as olivetol and/or olivetolic acid.

Analysis of the fermentation product may be performed by chromatography, preferably HPLC, to separate the fermentation product of interest to determine the concentration at one or more times during the incubation process. Microbial cultures and fermentation products can also be detected by photometric means (absorption, fluorescence).

The engineered microorganisms described herein achieve increased PHA yield. In some embodiments, the engineered microorganism described herein has achieved a yield of at least about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 times or higher or a range consisting of any two of the foregoing values in PHA production compared to appropriate unengineered or partially engineered microbial controls. In some embodiments, the engineered microorganism described herein has achieved a yield of at least about 0.1, 0.2, 0.3, 0.4, 0.5, 0.6, 0.7, 0.8, 0.9, 1.0, 1.1, 1.2, 1.4, 1.6, 1.8, 2.0, 2.2, 2.4, 2.6, 2.8, 3.0, 3.2, 3.4, 3.6, 3.8, 4.0, 4.0, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 350, 400, 450, 500, 550, 600, 650, 700, 750, 800, 850, 900, 950, 1000 mg/L or higher or a range consisting of any two of the foregoing values in the production of olivetol and/or olivetolic acid.

EXAMPLE

Hereinafter, the present invention will be described in detail by Examples. The Examples provided herein, however, are for illustrative purposes only and are not intended to limit the present invention.

The experimental methods used in the following Examples are conventional methods unless otherwise specified.

The materials, reagents and the like used in the following examples are commercially available unless otherwise specified.

The enzyme reagents used were purchased from New England Biolabs(NEB) Co., Ltd., the kits for plasmid extraction were purchased from TIANGEN Biotech(Beijing)Co., Ltd., and the kits for DNA fragment recovery were purchased from Omega, USA. The corresponding operation steps were strictly in accordance with the product instructions. All culture mediums were prepared with deionized water unless otherwise specified.

Formula of the culture medium:
  LB medium: 5 g/L Yeast Extract (purchased from OXID, UK, catalog No. LP0021), 10 g/L peptone (purchased from OXID, UK, catalog No. LP0042), 10 g/L NaCl, and the rest is water. pH was adjusted to 7.0-7.2, and the resultant was subjected to autoclaving.
  Shake flask fermentation medium: 1% palm oil, 1 g/L $NH_4Cl$, 10 mL/L trace element solution I, and 1 mL/L trace element solution II. Wherein, the composition of trace element solution I was 20 g/L $MgSO_4$ and 2 g/L $CaCl_2$. The composition of trace element solution II was 100 mg/L $ZnSO_4 \cdot 7H_2O$, 30 mg/L $MnCl_2 \cdot 4H_2O$, 300 mg/L $H_3BO_3$, 200 mg/L $CoCl_2 \cdot 6H_2O$, 10 mg/L $CuSO_4 \cdot 5H_2O$, 20 mg/L $NiCl_2 \cdot 6H_2O$, and 30 mg/L $NaMoO_4 \cdot 2H_2O$. The above reagents were purchased from Sinopharm Chemical Reagent Co., Ltd.
  Seed medium I: 10 g/L peptone, 5 g/L Yeast Extract and 3 g/L glucose.
  Seed medium II: 0.15% palm oil, 10 g/L peptone and 5 g/L Yeast Extract.
  Production medium: 1.0% palm oil, 9.85 g/L $Na_2HPO_4 \cdot 12H_2O$, 1.5 g/L $KH_2PO_4$, 3.0 g/L $NH_4Cl$, 10 mL/L trace element solution I and 1 mL/L trace element solution II. Wherein, the composition of trace element solution I was 20 g/L $MgSO_4$ and 2 g/L $CaCl_2$. The composition of trace element solution II was 100 mg/L $ZnSO_4 \cdot 7H_2O$, 30 mg/L $MnCl_2 \cdot 4H_2O$, 300 mg/L $H_3BO_3$, 200 mg/L $CoCl_2 \cdot 6H_2O$, 10 mg/L $CuSO_4 \cdot 5H_2O$, 20 mg/L $NiCl_2 \cdot 6H_2O$ and 30 mg/L $NaMoO_4 \cdot 2H_2O$. Wherein, the above reagents were all purchased from Sinopharm Chemical Reagent Co., Ltd.

Example 1: Construction of BPS-050

S1. Construction of *Ralstonia eutropha* ReΔphaCΔproC

*Ralstonia eutropha* Re0980 was used as an original strain to construct the *Ralstonia eutropha* ReΔphaCΔproC.

The *Ralstonia eutropha* Re0980 (hereinafter referred to as Re0980) is a *Ralstonia eutropha* with the genomic phaC gene knocked out, namely *Ralstonia eutropha* ReΔphaC, the recombinant *Ralstonia eutropha* strain Re0980 was deposited in the Guangdong Microbial Culture Collection Center (Address: 5/F, Building 59, No. 100 Courtyard, Xianlie Middle Road, Guangzhou, Institute of Microbiology, Guangdong Academy of Sciences, postal code: 510070) on Dec. 31, 2021 with a deposit number of GDMCC No: 62177.

PCR amplification was performed using the Re0980 genome as a template to obtain upstream and downstream homologous fragments proC-h1 and proC-H2 of proC gene, and proC Fp and proC Rp were ligated with the vector fragment by the Gibson Assembly method to obtain the recombinant plasmid pK18mobsacB-ΔproC. The primers used were as follows:

| Primer name | Primer sequence |
|---|---|
| proC-H1 Fp | tggtacccggccaagtctgcctacgtccaggaaggcgtcg |
| proC-H1 Rp | cggtttggccgcgcctcaatatcgagcatggagatccgtt |
| proC-H2 Fp | aacggatctccatgctcgatattgaggcgcggccaaac |
| proC-H2 Rp | caggatgtgacgagcggtgcccgttcttcaagcgcttc |
| proC Fp | ctggcggtttccaagaccg |
| proC Rp | gtgttgccgctcaatgcgc |

The recombinant plasmid pK18mobsacB-ΔproC was transformed into *Escherichia coli* S17-1, and then transformed into *Ralstonia eutropha* by a joint transformation method, and the positive clone was screened with LB plates supplemented with 0.2% proline containing both 200 μg/mL kanamycin and 100 μg/mL apramycin, taking advantage of the inability of the suicide plasmid to replicate in the host bacteria. The recombinant plasmid with homologous fragments in this positive clone was integrated into the specific position on the genome where H1 and H2 are located for the first homologous recombinant bacteria.

The first homologous recombinant bacteria were cultured on LB plates containing 100 mg/mL sucrose supplemented with 0.2% proline by plate streaking to obtain single clones, and from these single clones, clones without kanamycin resistance were screened and PCR was performed with primers proC Fp and proC Rp to identify the recombinant bacteria with proC gene knockout, and the recombinant bacteria obtained were *Ralstonia eutropha* ReΔphaCΔproC.

S2. Construction of a Stable Plasmid Containing a phaC Mutant Gene and a proC Gene Constructing a plasmid which can be stably inherited in *Ralstonia eutropha*, and on which a proC gene and a phaC mutant gene are loaded, wherein the specific operations are as follows:
  gene synthesis of proC gene with BsaI linker sequence, wherein the specific synthetic sequence is represented by SEQ ID NO: 4;
  gene synthesis of phaC mutant gene with a BsaI linker sequence, wherein the specific synthetic sequence is represented by SEQ ID NO: 5;
  gene synthesis of pSP plasmid with BsaI linker sequence, wherein the specific synthetic sequence is represented by SEQ ID NO: 6;
  the above three plasmids were subjected to Goldengate assembly, and the recombinant plasmid PSP-B-phaC-proC containing the phaC mutant and the proC gene was obtained.

S3. Construction of Recombinant Bacteria with a Specific Promoter Inserted Upstream of the phaJ4b Gene Step 1: PCR amplification was performed by using the ReΔphaCΔproC genome of *Ralstonia eutropha* obtained in S1 as a template, to obtain an upstream homologous fragment H1 of the promoter of phaJ gene by using phaJ-H1 Fp and phaJ-H1 Rp; the upstream homologous fragment H2 of the promoter of phaJ gene was obtained using phaJ-H2 Fp and phaJ-H2 Rp.

Step 2: gene synthesis of the promoter phaJ43 of phaJ gene:

```
phaJ43:
ATGCCTCCACACCGCTCGTCACATCCTGTTGCGTTCACTGGAATCCCACG

ATAGAGTTTGACCTGCGAGCAAGCTGTCACCGGATGTGCTTTCCGGTCTG

ATGAGTCCGTGAGGACGAAACAGCCTCTACAAATAATTTTGTTTAA.
```

Step 3: H1 and H2 obtained by PCR and the phaJ43 promoter were ligated with the vector fragment by the Gibson Assembly method to obtain the recombinant plasmid pK18mobsacB-phaJ43. The primers used were as follows.

| Primer name | Primer sequence |
|---|---|
| phaJ-H1 Fp | gctgggccgccgaagtgagcttcgacggcgtcttcgttcc |
| phaJ-H1 Rp | cgagcggtgtggaggcatctattcagtcagggatgcct |
| phaJ-H2 Fp | ctacaaataattttgtttaactgactgaataggaagagcaagc |
| phaJ-H2 Rp | ccctgatttccataaggcgccgcacgccgcgcggtgacgac |
| phaJ Fp | ttcgtggtctcggccgat |
| phaJ Rp | caaagtcactgggttcccg |

Step 4: the recombinant plasmid pK18mobsacB-phaJ43 was transformed into *E. coli* S17-1, and then the recombinant plasmid was transformed into *Ralstonia eutropha* by a joint transformation method, and the positive clone was screened with LB plates supplemented with 0.2% proline containing both 200 μg/mL kanamycin and 100 μg/mL apramycin, taking advantage of the inability of the suicide plasmid to replicate in the host bacteria. The recombinant plasmid with homologous fragments in this positive clone was integrated into the specific position on the genome where H1 and H2 are located for the first homologous recombinant bacteria.

The first homologous recombinant bacteria were cultured on LB plates containing 100 mg/mL sucrose supplemented with 0.2% proline by plate streaking to obtain single clones, and from these single clones, clones without kanamycin resistance were screened and PCR was performed with primers phaJ Fp and phaJ Rp to identify the recombinant bacteria of the corresponding size, and the recombinant bacteria obtained were *Ralstonia eutropha* ReΔphaCΔproC_phaJ43.

S4. Transformation of the Stable Plasmid pSP-B-phaC-proC into the Mutant Strain with the phaJ Promoter Inserted The recombinant plasmid pSP-B-phaC-proC constructed in S2 was transformed into *E. coli* S17-1, and then transformed into the *Ralstonia eutropha* ReΔphaCΔproC_phaJ43 constructed by S3 through a joint transformation method, and positive clone was screened with LB plates containing 250 μg/mL of kanamycin to obtain the recombinant *Ralstonia eutropha*, the strain was designated as BPS-050, and the recombinant *Ralstonia eutropha* was deposited in China General Microbiological Culture Collection Center with a deposit number of CGMCC No. 23600. This clone will carry the designed stable plasmid and it is no longer needed to supplement the medium with proline.

The colonies were observed on LB solid medium: the colonies are pale yellow, with neat edges, smooth and moist; with strong odor. Microscopic examination showed that the strain is Gram-negative, short-rod-shaped, and asporous.

The 16s RNA of the strain was further sequenced and the 16s RNA sequence was as previously described.

Example 2: Construction of a Strain Expressing phaC Mutant Gene in Genome

The phaC mutant gene with 20 bp homologous arm sequence was synthesized, the specific synthetic sequence is as represented by SEQ ID NO: 7. The recombinant plasmid pK18mobsacB-phaC was obtained by ligating phaC-H1, phaC mutant gene, and phaC-H2 to the pK18mobsacB plasmid using Gibson ligation.

The constructed recombinant plasmid pK18mobsacB-phaC was transformed into *E. coli* S17-1, and then transformed into H16 strain with the phaC gene knocked out by a joint transformation method, and positive clones were screened with LB plates containing 250 μg/mL of kanamycin to obtain recombinant *Ralstonia eutropha* ReΔphaC:: phaCac, designated as G-0.

Example 3: Construction of Recombinant *Ralstonia eutropha*

In the present Example, the phaJ43 promoter was introduced on the basis of Example 2, and the introduction method was the same as S3 of Example 1, to obtain the recombinant *Ralstonia eutropha* ReΔphaC_phaJ43, designated as G-43.

Comparative Examples 1-3

Comparative Examples 1-3 are the same as Example 1 except that:
(1) in Step 2 of S3, promoters phaJ210, phaJ183, and phaJ225 of the phaJ gene were synthesized, respectively:

```
phaJ210 (SEQ ID NO: 8):
ATGCCTCCACACCGCTCGTCACAtcctgttgcgtTCACTGGAATCCCAgt atACAGtTTGACCTGCGAGCAaGCTGTCACCGGATGTGCTTTCCGGTCTG

ATGAGTCCGTGAGGACGAAACAGCCTCTACAAATAATTTTGTTTAA phaJ183 (SEQ ID NO: 9):
ATGCCTCCACACCGCTCGTCACAtcctgttgcgtTCACTGGAATCCCAgt atagcatTTGACCTGCGAGCAaGCTGTCACCGGATGTGCTTTCCGGTCTG

ATGAGTCCGTGAGGACGAAACAGCCTCTACAAATAATTTTGTTTAA phaJ225 (SEQ ID NO: 10):
ATGCCTCCACACCGCTCGTCACAtcctgttgcgtTCACTGGAATCCCAgt ataccctTTGACCTGCGAGCAaGCTGTCACCGGATGTGCTTTCCGGTCTG

ATGAGTCCGTGAGGACGAAACAGCCTCTACAAATAATTTTGTTTAA.
```

(2) In Step 3 of S3, H1 and H2 obtained by PCR were ligated with the phaJ210, phaJ183 and phaJ225 promoters, and the vector fragment respectively through the Gibson Assembly method to obtain recombinant plasmids pK18mobsacB-phaJ210, pK18mobsacB-phaJ183 and pK18mobsacB-phaJ225.

(3) In Step 4 of S3, the recombinant plasmids pK18mobsacB-phaJ210, pK18mobsacB-phaJ183 and pK18mobsacB-phaJ225 were respectively transformed into *E. coli* S17-1, and then transformed into *Ralstonia eutropha* by a joint transformation method, and the positive clone was screened with LB plates supplemented with 0.2% proline containing both 200 μg/mL kanamycin and 100 μg/mL apramycin, taking advantage of the inability of the suicide plasmid to replicate in the host bacteria. The recombinant plasmid with homologous fragments in this positive clone was integrated into the specific position on the genome where H1 and H2 were located for the first homologous recombinant bacteria.

The first homologous recombinant bacteria were cultured on LB plates containing 100 mg/mL sucrose supplemented with 0.2% proline by plate streaking to obtain single clones, and from these single clones, clones without kanamycin resistance were screened and PCR was performed with primers phaJ Fp and phaJ Rp to identify the recombinant bacteria of the corresponding size, and the recombinant bacteria obtained were *Ralstonia eutropha* ReΔphaCΔproC_phaJ210, ReΔphaCΔproC_phaJ183 and ReΔphaCΔproC_phaJ225.

(4) In S4, the recombinant plasmid pSP-B-phaC-proC constructed in S2 was transformed into *E. coli* S17-1, and then transformed into the *Ralstonia eutropha* ReΔphaCΔproC_phaJ210, ReΔphaCΔproC_phaJ183 and ReΔphaCΔproC_phaJ225 constructed in S3 respectively by a joint transformation method, the positive clones were screened out by LB plates containing 250 μg/mL kanamycin, thus, the recombinant *Ralstonia eutropha* was obtained, and the strains were designated as P-210, P-183 and P-225.

Experimental Example 1: Shaking-Flask Test of the Fermentability of Mutant Strains The transformants obtained in Examples 1 to 3 and Comparative Examples 1 to 3 were subjected to plate streaking to obtain single clones of the mutant strains, the single clones were inoculated into a seed medium (4 ml) and cultured for 12 hours. The overnight culture was transformed to a 100 mL glass conical flask containing 10 mL of LB activation medium with a final inoculation amount by OD of about 0.1, and cultured for 8 hours at 30° C. and 200 rpm, and then transformed for culture. Polyester production culture was performed by inoculating the pre-culture seeds with a OD value between 6 and 7 into 250 ml shaking flask filled with 30 ml fermentation medium at 0.1 OD, and then adding 300 μl palm oil and a certain amount of emulsifier. After 48 hours, the fermentation was stopped and the fermentation broth was centrifuged to obtain bacteria. The bacteria were dried to a constant weight.

The weight of the dried bacteria was measured and recorded as dry weight. To the obtained dried cells was added about 100 ml of chloroform, and the mixture was stirred at room temperature for one day and night to extract polyester from the bacteria. After the bacterial residue was filtered off, the filtrate was concentrated by an evaporator to a total volume of about 30 ml, and then about 90 ml of hexane was slowly added and allowed to stand for 1 hour with slow stirring. The polyester was filtered out and dried under vacuum at 5CTC for 3 hours. The mass of the dried polyester was measured and the polyester content in the bacteria was calculated.

The test results of each strain are shown in table 1 below:

|  | Dry weight (g/L) | PHA proportion | 3HHx proportion |
| --- | --- | --- | --- |
| G-0 | 10.72 | 80.85% | 2.56% |
| G-43 | 10.15 | 81.59% | 11.21% |
| P-210 | 3.73 | 56.73% | 8.71% |
| P-183 | 3.83 | 48.71% | 10.94% |
| P-225 | 6.08 | 67.88% | 9.23% |
| BPS-050 | 10.34 | 82.21% | 8.15% |

The shaking-flask results revealed that the proportion of 3HHx in the metabolites of G-43 and BPS-050 was significantly increased after the use of the P43 promoter, while the fermentation capacity of the strains was higher than that of the control strain G-0, and there was room for further improvement in the fermentation performance after expression of the phaC mutant gene and the proC gene using the plasmid version. In contrast, the use of other promoter sequences with theoretically higher expression intensity did not correspondingly increase the yield but reduced the cell dry weight instead.

Experimental Example 2: Fermentation Tank Test

First, the strains of Example 1 and Example 3 preserved in glycerol tubes (1000 μL) were inoculated into seed medium I (20 ml) and subjected to 12 hours of primary seed culture. Next, 1% of the seed culture solution I was inoculated into the seed culture medium II for secondary seed culture. Then, the seed culture solution II was inoculated into a 2 L small-scale fermentor (T&J Bioengineering Co. Ltd.) filled with 1.1 L production culture medium at 10 v/v %. The operating conditions were a culture temperature of 30° C., a stirring speed of 800 rpm, and an aeration rate of 1 L/min, and the pH was controlled within the range of 6.7 and 6.8. A 28% aqueous ammonia solution was used for pH control. Palm oil was continuously used as a carbon source during the incubation, and the incubation time was 54 hours.

The detection method was the same as that in Experimental Example 1.

The culture results of each strain are shown in FIG. 1 and table 2:

| Strain number | Dry weight (g/L) | PHA proportion |
|---|---|---|
| G-0 | 201.64 | 80.73% |
| G-43 | 207.12 | 81.59% |
| P-210 | 120.47 | 53.77% |
| P-183 | 108.88 | 47.51% |
| P-225 | 170.77 | 67.09% |
| BPS-50 | 212.72 | 83.48% |

Compared with the control strain G-0, the recombinant strain BPS-050 obtained through gene editing has the advantages that on the basis of reaching a certain proportion of 3-hydroxycaproic acid, the cell dry weight is increased by 5.49% [(212.72−201.64)/201.64], and the PHA proportion is increased by 3.41% [(83.48%−80.73%)/80.73%], which is significantly improved compared with the control strain.

While preferred embodiments of the present invention have been shown and described herein, it should be apparent to a person skilled in the art that such embodiments are provided by way of example only. Numerous variations, changes and substitutions will now be contemplated by a person skill in the art without departing from the present invention. It should be understood that various alternatives to the embodiments of the present invention described herein may be employed in practicing the present invention.

What is claimed is:

1. A recombinant *Ralstonia eutropha*,
wherein a promoter for upregulating a phaJ gene is introduced into a genome of the recombinant *Ralstonia eutropha*,
wherein a sequence of the promoter for upregulating the phaJ gene is a phaJ43 promoter sequence of SEQ ID NO: 3,
wherein original genes phaC and proC in the genome of the recombinant *Ralstonia eutropha* are inactivated, a sequence of the original phaC gene is represented by SEQ ID NO: 1, a sequence of the original proC gene is represented by SEQ ID NO: 2,
wherein a plasmid capable of stably existing in *Ralstonia eutropha* is introduced into the recombinant *Ralstonia eutropha*, wherein the plasmid is loaded with an introduced phaC mutant gene and an introduced proC gene, wherein a sequence of the introduced phaC mutant gene is represented by SEQ ID NO: 5, the expression of the introduced phaC mutant gene enables the recombinant *Ralstonia eutropha* to synthesize 3-hydroxybutyrate-co-3-hydroxyhexanoate, a sequence of the introduced proC gene is represented by SEQ ID NO: 4,
wherein an original strain of the recombinant *Ralstonia eutropha* is *Ralstonia eutropha* Re0980, and a deposit number for the *Ralstonia eutropha* Re0980 is GDMCC No: 62177.

2. The recombinant *Ralstonia eutropha* according to claim 1, wherein the inactivation of the original genes phaC and proC is achieved by knocking out original genomic genes phaC and proC.

3. The recombinant *Ralstonia eutropha* according to claim 1, wherein the recombinant *Ralstonia eutropha* is strain BPS-050 with a deposit number of CGMCC No. 23600.

4. The recombinant *Ralstonia eutropha* according to claim 2, wherein the recombinant *Ralstonia eutropha* is strain BPS-050 with a deposit number of CGMCC No. 23600.

* * * * *

SEQUENCE LISTING

```
Sequence total quantity: 22
SEQ ID NO: 1               moltype = DNA  length = 1770
FEATURE                    Location/Qualifiers
source                     1..1770
                           mol_type = other DNA
                           organism = Ralstonia eutropha
SEQUENCE: 1
atggcgaccg gcaaaggcgc ggcagcttcc acgcaggaag gcaagtccca accattcaag    60
gtcacgccgg ggccattcga tccagccaca tggctgaat ggtcccgcca gtggcagggc    120
actgaaggca acggccacgc ggccgcgtcc ggcattccgg gcctggatgc gctggcaggc    180
gtcaagatcg cgccggcgca gctgggtgat atccagcagc gctacatgaa ggacttctca    240
gcgctgtggc aggccatggc cgagggcaag gccgaggcca ccgtccgct gcacgaccgg    300
cgcttcgccg gcgacgcatg gcgcaccaac ctcccatatc gcttcgctgc cgcgttctac    360
ctgctcaatg cgcgcgcctt gaccgagctg gccgatgccg tcgaggccga tgccaagacc    420
cgccagcgca tcccgcttcgc gatctcgcaa tgggtcgata cgatgtcgcc cgccaacttc    480
cttgccacca atcccgaggc gcagcgcctg ctgatcgagt cgggcggcga atcgctgcgt    540
gccggcgtgc gcaacatgat ggaagacctg acacgcggca agatctcgca gaccgacgag    600
agcgcgtttg aggtcggccg caatgtcgcg gtgaccgaag gcgccgtggt cttcgagaac    660
gagtacttcc agctgttgca gtacaagccg ctgaccgaca aggtgcacgc gcgcccgctg    720
ctgatggtgc cgccgtgcat caacaagtac tacatcctgg acctgcagcc ggagagctcg    780
ctggtgcgcc atgtggtgga gcaggacat acggtgtttc tggtgtcgtg gcgcaatccg    840
gacgccagca tggccggcag cacctgggac gactacatcg agcacgcggc catccgcgcc    900
atcgaagtcg cgcgcgacat cagcggccag gacaagatca acgtgctcgg cttctgcgtg    960
ggcggcacca ttgtctcgac cgcgctggcg gtgctggcga cgcggcgca gcacccggcc    1020
gccagcgtca cgctgctgac cacgctgctg gactttgccg acacgggcat cctcgacgtc    1080
tttgtcgacg agggccatgt gcagttgcgc gaggccacgc tgggcggcgg cgccggcgcg    1140
ccgtgcgcgc tgctgcgcgg ccttgagctg gccaatacct tctcgttctt gcgcccgaac    1200
gacctggtgt ggaactacgt ggtcgacaac tacctgaagg gcaacacgcc ggtgccgttc    1260
gacctgctgt tctggaacgg cgacgccacc aacctgccgg ggccgtggta ctgctggtac    1320
ctgcgccaca cctacctgca gaacgagctc aaggtaccgg gcaagctgac cgtgtgcggc    1380
gtgccggtgg acctggccag catcgacgtg ccgacctata tctacggctc gcgcgaagac    1440
catatcgtgc cgtggaccgc ggcctatgcc tcgaccgcgc tgctggcgaa caagctgcgc    1500
ttcgtgctgg gtgcgtcggg ccatatcgcc ggtgtgatca acccgccggc caagaacaag    1560
cgcagccact ggactaacga tgcgctgccg gagtcgcgc agcaatggct ggccggcgcc    1620
atcgagcatc acggcagctg gtggccggac tggaccgcat ggctggccgg gcaggccggc    1680
gcgaaacgcg ccgcgcccgc caactatggc aatgcgcgct atcgcgcaat cgaacccgcg    1740
cctgggcgat acgtcaaagc caaggcatga                                      1770

SEQ ID NO: 2               moltype = DNA  length = 837
FEATURE                    Location/Qualifiers
source                     1..837
                           mol_type = other DNA
                           organism = Ralstonia eutropha
SEQUENCE: 2
atgctcgata cccttacctt tggctttctc ggcggcggca acatggccac cgcactgatc     60
```

-continued

```
ggcggcctga tcgcccgcgg cgtgccggcc ggctcgatcc gcgtggtcga ccccttcccc  120
gaggcccagc aacgcctggc gcgcgacctc ggcgtgcatg ccgccggcgc gccggatgcc  180
gccttcggcg cctgcgacgt gctggtgctg gcggtcaagc gcagcagtt ccgcgacgcc  240
gcggcgcagc tgctgccgat cctgccggcc agcggcaagg gcaacctggt gatcagcgtg  300
gccgccggca tccggctgca ggacatggag cgctggctgg acgggcgcgc ccggctggtg  360
cgggcgatgc cgaacacgcc ggcgctggcc ggcatgggca tgaccgggct ggccgcgccg  420
gccgggctgt cggccgaaga ccgcgcgatc gccagcgcgg tggccgaggc cgtcggcaag  480
tgcgtatggg tggatgggga tgaccagatc gatgcggtca ccgccatttc cggcagtggg  540
ccggcctatg tcttctactt tatcgaagcg atggaacgcg ccgccaccga gctgggcctg  600
acggcggagc aaggccgcga actgcggta gaaaccttcc gtggcgctgc tacccctggcc  660
gggcagtctt ccgagccggt gtcgacgctg cgtgagcgcg tgacgtccaa gggcggcacg  720
acgtatgcgg cgctgacggc gatggaggct cgggcattg tgatgccctt cgtgcgcgcg  780
atgcatgctg ccgcggcgcg gggcaaggag atggggcgg agttcgggaa ggattga  837

SEQ ID NO: 3          moltype = DNA   length = 146
FEATURE               Location/Qualifiers
source                1..146
                      mol_type = other DNA
                      organism = Ralstonia eutropha
SEQUENCE: 3
atgcctccac accgctcgtc acatcctgtt gcgttcactg gaatcccacg atagagttg   60
acctgcgagc aagctgtcac cggatgtgct ttccggtctg atgagtccgt gaggacgaaa  120
cagcctctac aaataatttt gtttaa                                      146

SEQ ID NO: 4          moltype = DNA   length = 2025
FEATURE               Location/Qualifiers
source                1..2025
                      mol_type = other DNA
                      organism = Ralstonia eutropha
SEQUENCE: 4
ggtctcacaa ggtggacatc cttgtgcgtc atcgaggcga tgttgatccg gcgcatgtcg   60
ccgtggatcc gcaccatcgg cggcatgtcc gcggagagat gaagatcaga cgccttgttc  120
ttgacagcga aagccaatag ctgcgcgatg tccatctata atgaccccac cctagttatc  180
agtactttgc gtactttctt ttgtatgttc gccggattat gtctgtaatt gccgccaact  240
tgcaagccgt tcaccagcgc atcgcggcgg ccgcacaaca agcggcaga cagcccgccg  300
acatcgccct gctggcggtt ccaagaccgt tcccccgga ccgcataagg gccgcatacg  360
ccgccggaca ggtcgctttc ggcgaaaact acgtccagga aggcgtcgac aagatcgccg  420
cgctggccga cctgcgccac cgcctgcaat ggcatttcat cggcccgctg cagagcaaca  480
agacccgcct ggtggcggag catttcgact gggtgcagtc cgtcgaccgg ctcaggatcg  540
ccgagcggct gtcggcccag cgccggccg catggccgc gctgcaggtc tgcatccagg  600
tcaatatcag cggcgaagcc agcaagacg gcgtcgcccc ggcagaggtg cccggcctgg  660
cacatgccgt cgccgcgctg ccaggcctgc gcctgcgcgg gctgatggcc atccccgagc  720
ccgagcacga ccccgccgcg cagcgccgcc cgttcgccgc catgcgccgc atgctgccgg  780
cgctgcgcac cgacggcctg gacctcgaca cgctgtcgat gggcatgtcg ggcgacatgg  840
aagccgccat cgccgagggc gccacgctgg tgcggatcgg caccgccatt tcggagcgc   900
gccaatccc gtagtccggc gcgcccagtc cattcccttc aagccccca acggatcctc   960
atgctcgata cccttacctt tggctttctc ggcggcgga acatgccac cgcactgatc  1020
ggcggcctga tcgcccgcgg cgtgccggcc ggctcgatcc gcgtggtcga ccccttcccc  1080
gaggcccagc aacgcctggc gcgcgacctc ggcgtgcatg ccgccggcgc gccggatgcc  1140
gccttcggcg cctgcgacgt gctggtgctg gcggtcaagc gcagcagtt ccgcgacgcc  1200
gcggcgcagc tgctgccgat cctgccggcc agcggcaagg gcaacctggt gatcagcgtg  1260
gccgccggca tccggctgca ggacatggag cgctggctgg acgggcgcgc ccggctggtg  1320
cgggcgatgc cgaacacgcc ggcgctggcc ggcatgggca tgaccgggct ggccgcgccg  1380
gccgggctgt cggccgaaga ccgcgcgatc gccagcgcgg tggccgaggc cgtcggcaag  1440
tgcgtatggg tggatgggga tgaccagatc gatgcggtca ccgccatttc cggcagtggg  1500
ccggcctatg tcttctactt tatcgaagcg atggaacgcg ccgccaccga gctgggcctg  1560
acggcggagc aaggccgcga actgcggta gaaaccttcc gtggcgctgc tacccctggcc  1620
gggcagtctt ccgagccggt gtcgacgctg cgtgagcgcg tgacgtccaa gggcggcacg  1680
acgtatgcgg cgctgacggc gatggaggct cgggcattg tgatgccctt cgtgcgcgcg  1740
atgcatgctg ccgcggcgcg gggcaaggag atggggcgg agttcgggaa ggattgaggc  1800
gcggccaaac cgcgggcgct ctgacctggc cgccggccca tgtgaacgct ccctctccc  1860
gcaagcggga gagggagaa aaccagcggg atctaatcag cgaattgcat aagccaccgc  1920
cgtccccgca aacacacagg ccccccagcca gttgttatgc cggaacgccg cgaaacaccg  1980
catccggtcg cggtcacgaa tcagcgtgta atgatacctg agacc               2025

SEQ ID NO: 5          moltype = DNA   length = 2256
FEATURE               Location/Qualifiers
source                1..2256
                      mol_type = other DNA
                      organism = synthetic construct
SEQUENCE: 5
ggtctcatac ccaaaaattc atccttctcg cctatgctct ggggcctcgg cagatgcgag   60
cgctgcatac cgtccggtag gtcgggaagc gtgcagtgcc gaggcggatt cccgcattga  120
cagcgcgtgc gttgcaaggc aacaatggac tcaaatgtct cggaatcgct gacgattcgc  180
aggtttctcc ggcaagcata gcgcatggcg tctccatgcg agaatgtcgc gcttgccgga  240
taaaaggga gccgctatcg gaatggacgg aagccacggc cgcagcaggt gcggtcggagg  300
gcttccagcc agttccaggg cagatgtgcc ggcagaccct cccgctttgg gggaggcgca  360
agccgggtcc attcggatag catctcccca tgcaaagtgc cggccagggc aatgcccgga  420
gccggttcga atagtgacgg cagagagaga caatcaaatc atgagccaac catcttatgg  480
```

```
cccgctgttc gaggccctgg cccactacaa tgacaagctg ctggccatgg ccaaggccca    540
gacagagcgc accgcccagg cgctgctgca gaccaatctg gacgatctgg gccaggtgct    600
ggagcagggc agccagcaac cctggcagct gatccaggcc cagatgaact ggtggcagga    660
tcagctcaag ctgatgcagc acaccctgct caaaagcgca ggccagccga gcgagccggt    720
gatcaccccg gagcgcagcg atcgccgctt caaggccgag gcctggagcg aacaacccat    780
ctatgactac ctcaagcagt cctacctgct caccgccagg cacctgctgg cctcggtgga    840
tgccctggag ggcgtccccc agaagagccg ggagcggctg cgtttcttca cccgccagta    900
cgtctctgcc atggccccca gcaacttcct ggccaccaac cccgagctgc tcaagctgac    960
cctggagtcc ggcggccaga acctggtgcg cggactggcc ctcttggccg aggatctgga   1020
gcgcagcgcc gatcagctca acatccgcct gaccgacgaa tccgccttcg agctcgggcg   1080
ggatctggcc ctgaccccgg gccgggtggt gcagcgcacc gagctctatg agctcattca   1140
gtacagcccg actaccgaga cggtgggcaa gacacctgtg ctgatagtgc cgcccttcat   1200
caacaagtac tacatcatgg acatgcggcc ccagaactcc ctggtcgcct ggctggtcgc   1260
ccagggccag acggtattca tgatctcctg gcgcaaccgg ggctggcccg aggccaaat    1320
cgatctcgac gactacgtgg tggatgccgt catcgccgcc ctggacgcg  tggaggcggc   1380
caccggcgag cggagggtgc acggcatcgg ctactgcatc ggcggcaccg ccctgtcgct   1440
cgccatgggc tggctggcgg cgcggcgcca gaagcagcgg gtgcgcaccg ccaccctgtt   1500
cactaccctg ctggacttct cccagccccgg ggagcttgac atcttcatcc acgagcccat   1560
catagcggcg ctcgaggcgc aaaatgaggc caagggcatc atggacgggc gccagctggc   1620
ggtcagcttc agcctgctgc gggagaacag cctctactgg aactactaca tcgacagcta   1680
cctcaagggt cagagcccgg tggccttcga tctgctgcac tggaacagcg acagcaccaa   1740
tgtggcgggc aagacccaca acagcctgct gcgccgtcctc tacctggaga accagctggt   1800
gaaggggag ctcaagatcc gcaacacccg catcgatctc ggcaaggtga agaccccgt    1860
gctgctggtg tcggcggtgg acgatcacat cgccctctgg cagggcacct ggcagggcat   1920
gaagctgttt ggcggggagc agcgcttcct cctggcggag tccggccaca tcgccggcat   1980
catcaacccg ccggccgcca acaagtacgg cttctgccac aacggggcg aggccgagag   2040
ccccgagagc tggctggcag gggcgacgca ccagggcgcg tcctggtggc ccgagatgat   2100
gggctttatc cagaaccgtg acgaagggtc agagcccgtc cccgcgcggg tcccggagga   2160
agggctggcc cccgccccg gccactatgt caaggtgcgg ctcaaccccg tgtttgcctg   2220
cccaacagag gaggacgccg catgaccgct gagacc                             2256

SEQ ID NO: 6        moltype = DNA  length = 6752
FEATURE             Location/Qualifiers
source              1..6752
                    mol_type = other DNA
                    organism = synthetic construct
SEQUENCE: 6
cgtctcattt tcgccagata tcggtagcgg agtgtatact ggcttactat gttggcactg     60
atgagggtgt cagtgaaatg cttcatgtgg caggagaaaa aaggctgcac cggtgcgtca    120
gcagaatatg tgatacagga tatattccgc ttcctcgctc actgactcgc tacgctcggt    180
cgttcgactg cggcgagcgg aaatggctta cgaacgggc ggagatttcc tggaagatgc     240
caggaagata cttaacaggg aagtgagagg gccgcggcaa agccgttttt ccataggctc    300
cgcccccctg acaagcatca cgaaatctga cgctcaaatc agtggtggcg aaacccgaca    360
ggactataaa gataccaggc gtttccctg gcggctccct cgtgcgctct cctgttcctg    420
cctttcggtt taccggtgtc attccgctgt tatggccgcg tttgtctcat tccacgcctg    480
acactcagtt ccgggtaggc agttcgctcc aagctggact gtatgcacga accccccgtt    540
cagtccgacc gctgcgcctt atccggtaac tatcgtcttg agtccaaccc ggaaagacat    600
gcaaaagcac cactggcagc agccactggt aattgattta gaggagttag tcttgaagtc    660
atgcgccggt taaggctaaa ctgaaaggac aagttttggt gactgcgctc ctccaagcca    720
gttacctcgg ttcaaagagt tggtagctca gagaacccttc gaaaaccgc cctgcaaggc    780
ggttttttcg ttttcagagc aagagattac gcgcagacca aaacgatctc aagaagatca    840
tcttattaaa gggtcccaa taattacgat ttaaattgga tgaatgtcag ctactgggct    900
atctggacaa gggaaaacgc aagcgcaaag agaaagcagg tagcttgcag tgggcttaca    960
tggcgatagc tagactgggc ggttttatgg acagcaagcg aaccggaatt gccagctggg   1020
gcgccctctg gtaaggttgg gaagccctgc aaagtaaact ggatgcgtt cttgccgcca    1080
aggatctgat ggcgcagggg atcaagatct gatcaagaga caggatgagg atcgtttcgc   1140
atgattgaac aagatggatt gcacgcaggt tctccggccg cttgggtgga gaggctattc   1200
ggctatgact gggcacaaca gacaatcggc tgctctgatg ccgccgtgtt ccggctgtca   1260
gcgcaggggc gcccggttct ttttgtcaag accgacctgt ccggtgccct gaatgaactg   1320
caggacgagg cagcgcggct atcgtggctg gccacgacgg gcgttccttg cgcagctgtg   1380
ctcgacgttg tcactgaagc gggaagggac tggctgctat tgggcgaagt gccggggcag   1440
gatctcctgt catctcacct tgctcctgcc gagaaagtat ccatcatggc tgatgcaatg   1500
cggcggctgc atacgcttga tccggctacc tgcccattcg accaccaagc gaaacatcgc   1560
atcgagcgag cacgtactcg gatggaagcc ggtcttgtcg atcaggatga tctggacgaa   1620
gagcatcagg ggctcgcgcc agccgaactg ttcgccaggc tcaaggcgcg catgcccgac   1680
ggcgaggatc tcgtcgtgac ccatggcgat gcctgcttgc cgaatatcat ggtggaaaat   1740
ggccgctttt ctggattcat cgactgtggc cggctgggtg tggcggaccg ctatcaggac   1800
atagcgttgg ctacccgtga tattgctgaa gagcttggcg gcgaatgggc tgaccgcttc   1860
ctcgtgcttt acggtatcgc cgctcccgat tcgcagcgca tcgccttcta tcgccttctt   1920
gacgagttct tctgatcaat ttccgagaat gacgttctc agaaattgat ttgacttttg   1980
tccttttccg ctgcataacc ctgcttcggg gtcattatag cgattttttc ggtatatcca   2040
tcctttttcg cacgatatac aggattttgc caaagggttc gtgtagactt ccttggtgt    2100
atccaacggc gtcagccggg caggataggc gaagtaggcc cacccgcgag cgggtgttcc   2160
ttcttcactg tcccttattc gcacctggcg gtgctcaacg gaatcctgc tctgcgaggc    2220
tggccgtagg ccggccgcga tgcaggtggc tgctgaaccc cagccgaa ctgaccccac     2280
aaggccctgt acacgcctca aaggacggg agtgggacag cgtagccata gtccgagccg   2340
aagagacaat cgttcccgac agcgaaagcc cagaaagcga agaaaggcgc ctcttctacg   2400
tcgccgtcac gcgcgccagg gattgcctgt ttatctcaac ggcgaagaag aacccgacct   2460
cgcgcttcgt ccttgaggct ggcctaagcc ttacttcctg aggcgcgcat tctttgtgcg   2520
```

```
ttatatggca ctttcgtaga attcctcgcc ttttacttta acaacgaccg gtaagtaccg  2580
ggggaacagc tcgatctctc gggtacaaca ggcacaaagt taacttgcgt atacgtctaa  2640
gggccgctaa ccttcacggc aacgcaaccg cggacgtcat ttttgccgaa aacggttgca  2700
cgatccaccg gcggttccgg tgaacagctt aaaggttttt gaaccgaatg gatatcaagc  2760
tagcccaccc cagcaagacg acgcctgagg atttgaagca gttggcaaat ctctccgcgg  2820
tgatgctgca gaaaattcgg gatgagatgc tggagccatt tcctcggaag gaagccccgc  2880
tgatcccgtc tggccgccta caagaattgt gtggcatcga caaaacgcgg atgaaccggt  2940
ccctcaaaaa gggggatctc cctcaggcc agcaatcgcg acccggtgca gtgcgctatt  3000
tcagcctcag cgaggcaatg caatggatcc gagcggaact taagcctgtc ccgcgaaggg  3060
gaccaggtaa agtcattgca gttgcgaact tcaagggcgg tgtcacgaag accactatgt  3120
ccaccctcct ctgccagggc ttgagtctgc ggcgaggtcg gaaggtgtgc cacgttgatc  3180
tggatccgca gggaagcgca accacgctgt atggcatcaa tccacatgcc gaggtgtcgt  3240
ccgaaaacac cattatgccg ctcatcgagg cgtatttggc gggcgagtcc ttcgatatgc  3300
gagggcttcc tcaggagact tactggccta acctggattt gattccttcg tctactgagc  3360
ttttcaacgc ggagtttatg cttccggctc gggcgacggc agaggaaggc catattccgt  3420
tcgagcgcgt gttaagtaac ggcctcgatt cgttgaaaga cgaatatgac tacatcatcc  3480
tcgacacggc tcctacccte agctacctga ccatcaacgc gattttcgct gccgatggcg  3540
tcatcgtacc ggtggtcccg gacaccttgg cttttcgcgt c tatggtccag ttctggcaac  3600
tcttctcgga cctagtaaca ggcatggaag agcagagcga gggatctaaa aaggagttcg  3660
actttctcga tgttctcatg acacgcatgg agaaaaagaa cgctcctcgc ctggtggcag  3720
actggattcg cggcgtctat gggtcgcgcg tgctgccgat tgatcccct gagacggacc  3780
tcgcccgtaa cagcagcatt caatttcgca cggtctatga cctctcctct agcgaggcga  3840
acaccgagac gatgcgacgc attcgccaac cctgcgatga gtttgtcgac tatgtggacg  3900
acaaggtcag cgcgctttgg caaggaattg aagaatgagt ttgagagaaa agcttgccgc  3960
aaaggctggg aacatcaagg tcacggcgga agacttggag aaagccgctg cgcgcggtcc  4020
gcaagcgccg cgaactgcgc ccggtcagtt aatgcatatg caaggggaagg ttgagcgaca  4080
ggctaacgag atcgcgcaac taagagcaga acttgagtcg gcccgcgtca gcggcggcgc  4140
agtggatgtg cctatcgacc aactgcatga ggtcccaggc cgcagacgct tcatgcctcc  4200
cgagaagtat gtcgaattga gggaaaacct caggcacaac aagctcgttc atcctgtgat  4260
tgtatgccct cggcctgcgg gaggcttcga gattgtctcc gggcatcacc ggacagacga  4320
gtaccgcgag cttgggcgcg atcacatacg ctgcgtgctc ggcgaactta gttcagacga  4380
ggctgacacg ggcgcgttct acgcgaacct tatgcagtca gatttaacgg atttcgagaa  4440
gtttcggaag ttcgacgaac tgctgcttcg cagcccagac aagactcaag ccgcaatagc  4500
tgaacaggct ggtgtacctg tctcgactct ctcagagatt ttgtcgttcc ggaacttgtc  4560
tcccggagtc ctaagccttc tcgatagccg cccgacctg ctcgggtcga atgctggcgc  4620
cgagttggca agggcgacca agacggtcg cggggatcgg gtcgtcgaag cggttaagtt  4680
gttggccgag aagaagatcg atcaacagca ggccgtacgg atgactaagg ccgagcaggt  4740
taagaccagg cctgccgcat ctaccggctt caaaatcaag gcgggaaagg cgacttggtg  4800
cgatgttcgt atcgcaaaga aagtcatgcg cattgagttc cgcagcgagg aagaagcgga  4860
agcggcccaa tcggccattc gcgaacatct ggaagggtta gctaaagctg cgtcggaaga  4920
cgcaaaaagc taagtgcttg tttttttaagg acttcgtact acgaatcgag gttttaagcc  4980
atgtctagac tgtaatccta caaaaacaaa agcccacggc ggcaaccgtg ggcttttgag  5040
aacttcaagc tgaccagttt cccggccgct acacaccgaa ccactcgac atggattcgt  5100
tagtcggagt gtagcggaac gcgaacctga gtcaagcgac ttcaaccatt ttttacgaat  5160
gggaaggtca tatgactttc gcgcaacgct ccgttgctgg cgaggatgtt gctcgcccac  5220
aaaaacacct taaccagaca gacgctcgta ttgctccggc gcccaagcgc ctcaaacgca  5280
agactatcga agcagtcgag cgcgcaactc gaatcgtcag gatcgggcgt agcgcccgat  5340
cagctcttgc cgcccctcgcc cgcacgcgca ataacgatga ccccaccggt aagatcttta  5400
agcaccggga aacgctttgt gccgaaaccg gaatgtcgcc ggctacttgg taccgtgctc  5460
aacgagaact gctcgacttg ggcctaatta ccgtcgacgt tcaagttcgg aagcgatttg  5520
gccgattcgc aggagcctac atttacctga cggaaaaagc gacggagatg ctcggcttaa  5580
gctcgcgaaa agaagaagaa accacgggta cgggcgagga cgacacgcg cagctcggcg  5640
agccggccgt tccaccaccc tcttctatgg cgcaaccgtc tctcaaaacg agagtcctgt  5700
ttacagaaga tcgtgtccca tactccttc aaaaaagaca gcaggatcgg ctcccccagg  5760
acctgacacg tctgcgcggc ctgggtcttg atgtaaattt aatttttgg ttgatgcgaa  5820
aggctaaaga gcaaggccac tttctctcag atgtcgtaag cgcgacatgg gagagtcttg  5880
cgaaagcacg cgtgccaaaa gcgtatctgc ttgccctact caccgcccgc accgatttca  5940
gtgctgtctg caaagcaaag gcactcaaag aagacaaagc ccgaatccaa gtgcaggacc  6000
gcgatttcgt gcgttcgata ctcgcagggg cagccggca gtgtttcgtg gacgaaaag  6060
gcaaccattt cgaagtcgaa agcgacggaa gctcagtgct tgtcaccgag gtccaaagtg  6120
cggtcacttc ccgcttggta ggaacttccc tcgccgaatt tgcaaggcga ctacacgctg  6180
gtgcgtacca gaaagctgag gtctacgctg ctcccccagag agcaagcggc cggctcgaga  6240
aacgggggaaa ggaggcggct tcgacgttat cggcgttgcg agcgatgctg cgcgaccgca  6300
ggtcagccaa cgccggcaaac acgacgaaca atgctcatgc catggcctag ggtgtgtttt  6360
gcgctgaaag tctagggcgg cggatttgtc ctactcagga gagcgttcac cgacaaacaa  6420
cagataaaac gaaaggccca gtctttcgac tgagcctttc gttttatttg atgcctttaa  6480
ttaaagcgga taacaatttc acacaggaga gtgaagagct tttgctcttc atccaagcga  6540
gaccaaaagg tctcgccgcg acccattacc gcctttgagt gagcgtcgtg actgggaaaa  6600
ccctggcgac tagtcttgga ctcctgttga tagatccagt aatgacctca gaactccatc  6660
tggatttgtt cagaacgctc ggttgccgcc gggcgtttttt tattggtgag aatccagtca  6720
atttccgaga atgacagttc tcagaaattg aa                                  6752
SEQ ID NO: 7        moltype = DNA   length = 1825
FEATURE             Location/Qualifiers
source              1..1825
                    mol_type = other DNA
                    organism = synthetic construct
SEQUENCE: 7
ggcagagaga caatcaaatc atgagccaac catcttatgg cccgctgttc gaggccctgg  60
```

```
cccactacaa tgacaagctg ctggccatgg ccaaggccca gacagagcgc accgcccagg    120
cgctgctgca gaccaatctg gacgatctgc gccaggtgct ggagcagggc agccagcaac    180
cctggcagct gatccaggcc cagatgaact ggtggcagga tcagctcaag ctgatgcagc    240
acaccctgct caaaagcgca ggccagccga gcgagccggt gatcaccccg gagcgcagcg    300
atcgccgctt caaggccgag gcctggagcg aacaaccgac ctatgactac ctcaagcagt    360
cctacctgct caccgccagg cacctgctgg cctcggtgga tgccctggag ggcgtccccc    420
agaagagccg ggagcggctg cgtttcttca cccgccagta cgtctctgcc atggccccca    480
gcaacttcct ggccaccaac cccgagctgc tcaagctgac cctggagtcc ggcggccaga    540
acctggtgcg cggactggcc ctcttggccg aggatctgga gcgcagcgcc gatcagctca    600
acatccgcct gaccgacgaa tccgccttcg agctcgggcg ggatctggcc ctgaccccgg    660
gccgggtggt gcagcgcacc gagctctatg agctcattca gtacagcccg actaccgaga    720
cggtgggcaa gacacctgtg ctgatagtgc cgcccttcat caacaagtac tacatcatgg    780
acatgcggcc ccagaactcc ctggtcgcct ggctggtcgc ccagggccag acggtattca    840
tgatctcctg gcgcaaaccg ggcgtggccc aggcccaaat cgatctcgac gactacgtgg    900
tggatgcgct catcgccgcc ctggacggcg tggaggcggc caccggcgag cgggaggtgc    960
acggcatcgg ctactgcatc ggcggcaccg ccctgtcgct cgccatgggc tggctggcgg   1020
cgcggcgcca gaagcagcgg gtgcgcaccg ccaccctgtt cactaccctg ctggacttct   1080
cccagcccgg ggagcttggc atcttcatcc acgagcccat catgcgggcg ctcgaggcgc   1140
aaaatgaggc caagggcatc atggacgggc gccagctggc ggtcagcttc agcctgctgc   1200
gggagaacag cctctactgg aactactaca tcgacagcta cctcaagggt cagagcccgg   1260
tggccttcga tctgctgcac tggaacagcg acagcaccaa tgtggcgggc aagacccaca   1320
acagcctgct gcgccgtctc tacctggaga accagctggt gaaggggggag ctcaagatcc   1380
gcaacacccg catcgatctc ggcaaggtga agacccctgt gctgctggtg tcggcggtgg   1440
acgatcacat cgccctctgg cagggcacct ggcagggcat gaagctgttt ggcggggagc   1500
agcgcttcct cctggcggag tccggccaca tgccggcat catcaacccg ccggccgcca   1560
acaagtacg cttctggcac aacgggccg aggccgagag cccggagagc tggctggcag   1620
gggcgacgca ccaggcggc tcctggtggc ccgagatgat gggctttatc cagaaccgtg   1680
acgaagggtc agagcccgtc cccgcgcggg tccggagga agggctgccc ccgccccg    1740
gccactatgt caaggtgcgg ctcaaccccg tgtttgcctg cccaacagag gaggacgccg   1800
catgacgctt gcatgagtgc cggcg                                         1825

SEQ ID NO: 8            moltype = DNA   length = 146
FEATURE                 Location/Qualifiers
source                  1..146
                        mol_type = other DNA
                        organism = synthetic construct
SEQUENCE: 8
atgcctccac accgctcgtc acatcctgtt gcgttcactg gaatcccagt atacagtttg     60
acctgcgagc aagctgtcac cggatgtgct ttccggtctg atgagtccgt gaggacgaaa    120
cagcctctac aaataatttt gtttaa                                         146

SEQ ID NO: 9            moltype = DNA   length = 146
FEATURE                 Location/Qualifiers
source                  1..146
                        mol_type = other DNA
                        organism = synthetic construct
SEQUENCE: 9
atgcctccac accgctcgtc acatcctgtt gcgttcactg gaatcccagt atagcatttg     60
acctgcgagc aagctgtcac cggatgtgct ttccggtctg atgagtccgt gaggacgaaa    120
cagcctctac aaataatttt gtttaa                                         146

SEQ ID NO: 10           moltype = DNA   length = 146
FEATURE                 Location/Qualifiers
source                  1..146
                        mol_type = other DNA
                        organism = synthetic construct
SEQUENCE: 10
atgcctccac accgctcgtc acatcctgtt gcgttcactg gaatcccagt ataccctttg     60
acctgcgagc aagctgtcac cggatgtgct ttccggtctg atgagtccgt gaggacgaaa    120
cagcctctac aaataatttt gtttaa                                         146

SEQ ID NO: 11           moltype = DNA   length = 40
FEATURE                 Location/Qualifiers
source                  1..40
                        mol_type = other DNA
                        organism = synthetic construct
SEQUENCE: 11
tggtacccgg ccaagtctgc ctacgtccag gaaggcgtcg                           40

SEQ ID NO: 12           moltype = DNA   length = 40
FEATURE                 Location/Qualifiers
source                  1..40
                        mol_type = other DNA
                        organism = synthetic construct
SEQUENCE: 12
cggtttggcc gcgcctcaat atcgagcatg gagatccgtt                           40

SEQ ID NO: 13           moltype = DNA   length = 38
FEATURE                 Location/Qualifiers
```

```
                               -continued source               1..38
                     mol_type = other DNA
                     organism = synthetic construct
SEQUENCE: 13
aacggatctc catgctcgat attgaggcgc ggccaaac                          38

SEQ ID NO: 14        moltype = DNA   length = 38
FEATURE              Location/Qualifiers
source               1..38
                     mol_type = other DNA
                     organism = synthetic construct
SEQUENCE: 14
caggatgtga cgagcggtgc ccgttcttca agcgcttc                          38

SEQ ID NO: 15        moltype = DNA   length = 19
FEATURE              Location/Qualifiers
source               1..19
                     mol_type = other DNA
                     organism = synthetic construct
SEQUENCE: 15
ctggcggttt ccaagaccg                                               19

SEQ ID NO: 16        moltype = DNA   length = 19
FEATURE              Location/Qualifiers
source               1..19
                     mol_type = other DNA
                     organism = synthetic construct
SEQUENCE: 16
gtgttgccgc tcaatgcgc                                               19

SEQ ID NO: 17        moltype = DNA   length = 40
FEATURE              Location/Qualifiers
source               1..40
                     mol_type = other DNA
                     organism = synthetic construct
SEQUENCE: 17
gctgggccgc cgaagtgagc ttcgacggcg tcttcgttcc                        40

SEQ ID NO: 18        moltype = DNA   length = 38
FEATURE              Location/Qualifiers
source               1..38
                     mol_type = other DNA
                     organism = synthetic construct
SEQUENCE: 18
cgagcggtgt ggaggcatct attcagtcag ggatgcct                          38

SEQ ID NO: 19        moltype = DNA   length = 43
FEATURE              Location/Qualifiers
source               1..43
                     mol_type = other DNA
                     organism = synthetic construct
SEQUENCE: 19
ctacaaataa ttttgtttaa ctgactgaat aggaagagca agc                    43

SEQ ID NO: 20        moltype = DNA   length = 41
FEATURE              Location/Qualifiers
source               1..41
                     mol_type = other DNA
                     organism = synthetic construct
SEQUENCE: 20
ccctgatttc cataaggcgc cgcacgccgc gcggtgacga c                      41

SEQ ID NO: 21        moltype = DNA   length = 18
FEATURE              Location/Qualifiers
source               1..18
                     mol_type = other DNA
                     organism = synthetic construct
SEQUENCE: 21
ttcgtggtct cggccgat                                                18

SEQ ID NO: 22        moltype = DNA   length = 19
FEATURE              Location/Qualifiers
source               1..19
                     mol_type = other DNA
                     organism = synthetic construct
SEQUENCE: 22
caaagtcact gggttcccg                                               19
```